United States Patent [19]

Hama

[11] 4,153,356

[45] May 8, 1979

[54] LIGHT SOURCE APPARATUS FOR ENDOSCOPE

[75] Inventor: Hiroyuki Hama, Higashimurayama, Japan

[73] Assignee: Olympus Optical Co., Ltd., Tokyo, Japan

[21] Appl. No.: 833,493

[22] Filed: Sep. 15, 1977

[30] Foreign Application Priority Data

Sep. 16, 1976 [JP] Japan ................................ 51-110973

[51] Int. Cl.² ......................... G03B 29/00; A61B 1/04
[52] U.S. Cl. ........................................... 354/62; 128/8
[58] Field of Search ...................... 354/62, 63, 75, 76, 354/32, 33, 126; 128/6, 8

[56] References Cited

U.S. PATENT DOCUMENTS 3,599,630  8/1971  Sato et al. .......................... 354/62 X

FOREIGN PATENT DOCUMENTS 21341 12/1972 Japan.
41487  3/1977 Japan.

Primary Examiner—Michael L. Gellner

Attorney, Agent, or Firm—Lerner, David, Littenberg & Samuel

[57] ABSTRACT

A light source apparatus for endoscopes is provided which automatically controls an illuminating source used in an endoscope for photography. The apparatus comprises an optical system for directing the flux of illuminating rays from a source lamp to a bundle of optical fibres which is used to transmit illuminating light through the endoscope, including a lamp current control circuit for establishing an input current to the lamp at a maximum, a minimum or any other intermediate value, a first switch synchronized with the initiation of the exposure of a photographic film for switching the input current to the lamp to its maximum value and for commencing the calculation of the amount of exposure given to the film to produce an exposure stop signal when a given amount of exposure is reached, and a second switch responsive to the exposure stop signal to switch the input current to the lamp from the maximum to the minimum value and for terminating the exposure by bringing a light shield member into the path of illuminating light. The apparatus is adapted for use with any one of three distinct types of endoscopes.

15 Claims, 11 Drawing Figures

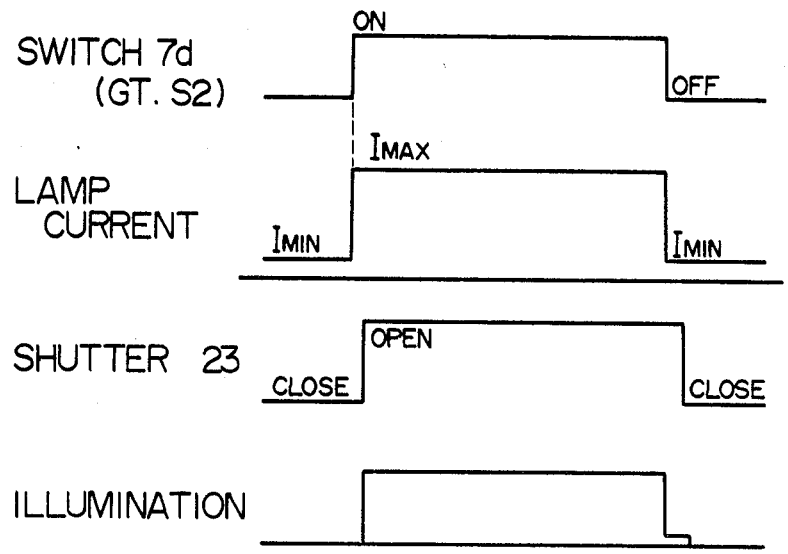
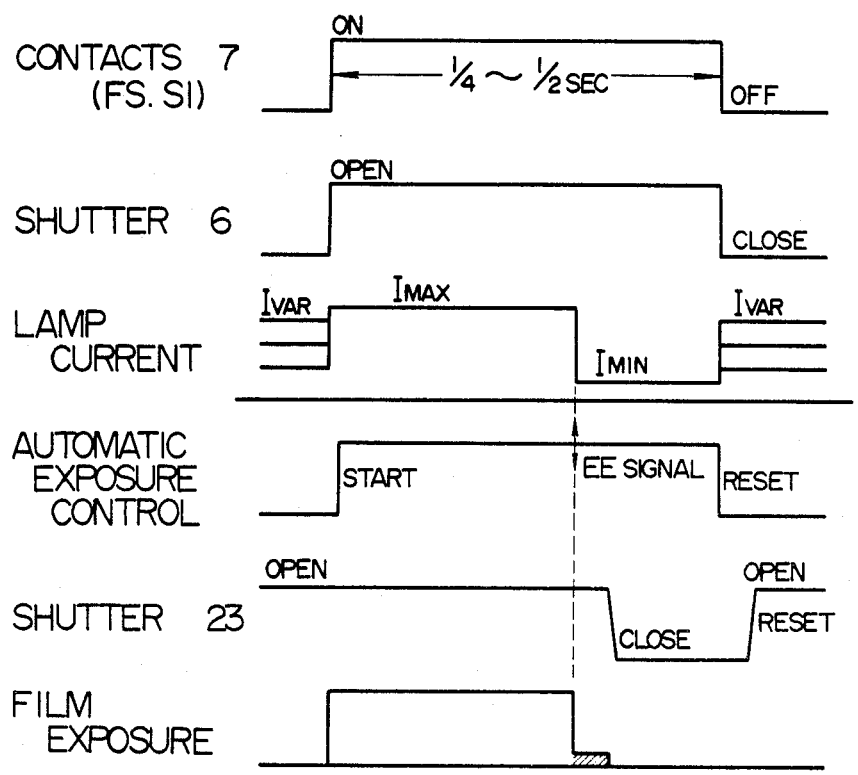

LIGHT SOURCE APPARATUS FOR ENDOSCOPE

BACKGROUND OF THE INVENTION

The invention relates to a light source apparatus for an endoscope, and more particularly, to such a multipurpose apparatus for use with a variety of endoscopes.

Endoscopes can be classified into three types according to the synchronization techniques of the still photography, namely, fibrescopes with external still camera, gastrocameras with shutter and viewfinder, and gastrocameras without shutter and viewfinder.

As illustrated in FIG. 1, a fibrescope is essentially comprised of a light guide 1 (a bundle of optical fibres for transmitting illuminating light), and an image guide 2 (a bundle of optical fibres for transmitting a light image) provided with observation lenses 2a, 2b. This permits a normal observation, and where it is desired to take a still photograph of an object 3 such as an affected part within a cavity, an external still camera 4 is attached to the proximal end of the image guide 2 outside the cavity. The still camera 4 comprises a single lens reflex camera of the type commonly used, including a film 5, shutter 6 and synchronization contacts 7. For automatic exposure control of the still photography, there may be provided a half mirror 8 and a light receiving photoelectric transducer element 9 which is connected with an automatic exposure control circuit.

As a feature of the endoscope, the opening and closing of the shutter is not always necessary to perform an exposure control of the film, which may also be achieved by the interruption of illuminating light. For this reason, the exposure control system is contained within a light source apparatus. To this end, the light source apparatus is connected with the fibrescope through a multi-function connector 10 which permits simultaneous connection of optical, electrical and pneumatic (not shown) media between the apparatus and the endoscope. The connector 10 is also used in a gastrocamera to be described later, permitting a common use of the same light source apparatus with the fibrescope. The fibrescope may also be utilized for viewing an affected part through a cine camera or a television camera. In such instance, the cine camera or television camera replaces the still camera 4. The transducer element 9 may be utilized during such use to control the illumination of a film surface to a constant value, by adjusting the light source.

A gastrocamera includes a camera mechanism mounted in the distal end of an endoscope and which can be remotely operated from the exterior to achieve a photographing and a film winding operation. As mentioned previously, there are two kinds of gastrocameras, those including and not including a shutter and a viewfinder. In either kind of gastrocamera, there is no governor for controlling the shutter speed of the camera, and the exposure period is controlled by a manual operation, so that the use of synchronized photographing well known in the art of ordinary cameras is precluded.

Where an automatic exposure control is intended, the calculation of the exposure period and the synchronization of the film exposure are the two most important factors requiring a special synchronizing arrangement in the light source. Usually, a film used in the gastrocamera has a width on the order of four or five millimeters, and hence a commercially available ordinary film cannot be directly used in the gastrocamera. Special film requirements, quantity sold and the developing process required limit the variety of films, including those used with daylight and those used with tungsten lamps. When providing one of these films and using a light source of the opposite kind, it is necessary to correct the color temperature by inserting a color conversion filter. Also, it may be necessary to use a film speed constant which is different from that used with the fibrescope. Additionally, the absence of a shutter speed controlling governor may cause an extended exposure period when taking a picture in dark place, which may result in a blurring of the image to produce an unusable photograph. Thus it will be seen that the light source apparatus must accommodate for these requirements, a feature requiring a special attention to the gastrocamera in contradistinction to the fibrescope.

FIG. 2 shows an exemplary gastrocamera with shutter and viewfinder while FIG. 3 illustrates an exemplary gastrocamera without shutter and viewfinder. In these Figures, corresponding elements are designated by like reference characters. In either arrangement, the gastrocamera includes a light guide 1A for transmitting illuminating light to an object 3 such as an affected part in a cavity, the reflected light of which is passed through an objective 2c onto a film 5A for exposure. The film 5A is drawn from a cartridge 16, and a film winding takes place through a string 12 by a remote control. The connection with the light source apparatus is accomplished through a multi-function connector 10 in a manner similar to that of the fibrescope.

The gastrocamera of FIG. 2 includes an image guide 2A which permits a normal viewing operation. A shutter 6a is disposed in front of the film 5A since otherwise the viewing light will cause an exposure of the film 5A. The shutter 6a is adapted to be remotely controlled by a string 11 which is disposed around a drum 13. A pair of switch operating projections 14a, 14b are mounted on the drum 13 for cooperation with synchronizing switches 7a, 7b. The arrangement is such that the switch 7a is actuated by the projection 14a immediately before the shutter 6a begins to open while the projection 14b actuates the switch 7b immediately after the shutter 6a has opened. These switches are maintained in their actuated position until the shutter 6a returns after the completion of a photographing operation. The two synchronization signals generated by the switches 7a, 7b serve as the means for clearly defining the period during which the shutter continues to move inasmuch as the shutter 6a is manually operated. These signals are effectively used when the gastrocamera is coupled with the light source apparatus according to the invention.

A combination of half mirror 8 and photoelectric transducer element 9 operates in a manner similar to that of the fibrescope for the purpose of automatic exposure control. A resistor 15 is connected with the multifunction connector 10 for discriminating the kind of the endoscope, and is effective to indicate to the light source unit that the endoscope coupled therewith is one having a shutter and viewfinder.

In the gastrocamera of FIG. 3, neither the image guide nor the shutter as shown in FIG. 2 are present. This is because no viewing operation is performed and hence there is no need for a shutter which shields light from the film 5A. A synchronizing switch 7c is closed when taking a still photograph to permit an illumination of the object 3 through the light guide 1A. The reflected light from the object impinges on the transducer element 9a to control the exposure period. A switch 7d is provided to enable the detection of the position of the inserted gastrocamera. Because the gastrocamera of FIG. 3 is not provided with a viewfinder which would normally indicate the depth of the camera when inserted into a cavity in a human body, a temporary illumination is activated through the switch 7d while observing the surface of the physical body of a patient whose clothes have been removed so that the camera position within the cavity may be located by viewing a bright region along the body through which the light leaks.

The synchronizing switch 7c is interlocked with a film winding mechanism, not shown, which feeds the film 5A one frame for each closure thereof. However, the switch 7d operates alone, minimizing a waste in the film which occurs as a result of its exposure by the locating illumination. A short circuit 15d across selected pins of the multi-function connector 10 is shown, and is provided for the discrimination of the kind of the endoscope, serving to indicate to the light source apparatus that the gastrocamera connected therewith has no shutter and viewfinder.

As will be noted from the foregoing description, the synchronization technique for still photography is different for each of the described kinds of the endoscopes even though any of these endoscopes can be connected with the light source apparatus through the multi-function connector. However, the adjustment of illumination, automatic exposure control for the still photography as well as the cine and television cameras vary from endoscope to endoscope, requiring a manual intervention and causing inconveniences.

SUMMARY OF THE INVENTION

In view of the foregoing, it is an object of the invention to provide a light source apparatus which may be used with any one of the described three kinds of endoscopes employing different synchronization techniques for the still photography and which provides an improvement in the adjustment of illumination and the automatic exposure control for the still photography as well as the cine and television cameras while permitting an automatic selection, without manual intervention, of an optical filter or constants used in an automatic exposure control which must be used with a specific endoscope selected.

The light source apparatus of the invention can be used with any one of three distinct kinds of endoscopes. The apparatus includes a discharge lamp as a light source, the current supply to which can be reduced to a selected level in response to an exposure stop signal, thereby substantially eliminating an exposure error. The apparatus can be automatically established in a given mode corresponding to one of the three distinct kinds of endoscopes, and when a given mode is established, the selection and movement of a color conversion filter into the optical path as well as the setting of film speed can be made without requiring manual intervention. The use of the multi-function connector for the coupling between the endoscope and the apparatus avoids a complication in a setting and panel operation. This is especially important in emergencies where simplicity and reliability of operation is required.

Additionally, the viewing and the automatic exposure with a cine and a television camera can be improved over the conventional servo aperture control which is characterized by a slow response, and provides a stabilized control.

Direct control of the lamp current has been impossible in the prior art without a resulting change in the color temperature where the incandescent lamp is used. However, this is made possible in the present invention by the use of an arc discharge lamp.

Where an endoscope is used having no governor for controlling the shutter speed, the photographing operation is forcedly interrupted above a given exposure period by the provision of an internally housed timer in order to limit a blurring of the resulting photograph. In the prior practice, a confusion is found among users to determine the time at which the shutter release is to be returned.

When the apparatus is used with a gastrocamera having no viewfinder, a switch which is independent from the film winding operation may be operated to permit an illumination for a given time interval in order to permit the illumination to be utilized for locating the position of the gastrocamera introduced into the cavity of a human body. In this manner, the invention simplifies the operation during the diagnosis using the endoscope while avoiding inadvertent setting or use, thus affording a great contribution to the progress of the medical art.

BRIEF DESCRIPTION OF THE DRAWINGS

FIGS. 8 to 11 are timing diagrams illustrating the illuminating operation for locating the position of a gastrocamera having no shutter and viewfinder, a photographing operation with a fibrescope, a photographing operation of a gastrocamera having shutter and viewfinder, and a photographing operation of a gastrocamera having no shutter and viewfinder.

DESCRIPTION OF PREFERRED EMBODIMENT

Figure 3:
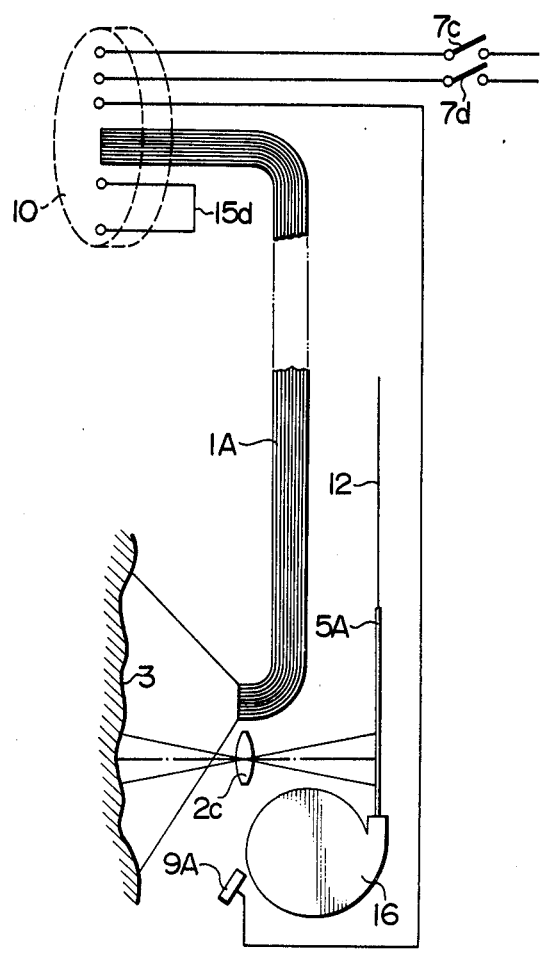
FIG. 3 is a schematic view of a gastrocamera having no shutter and viewfinder.
Figure 4:
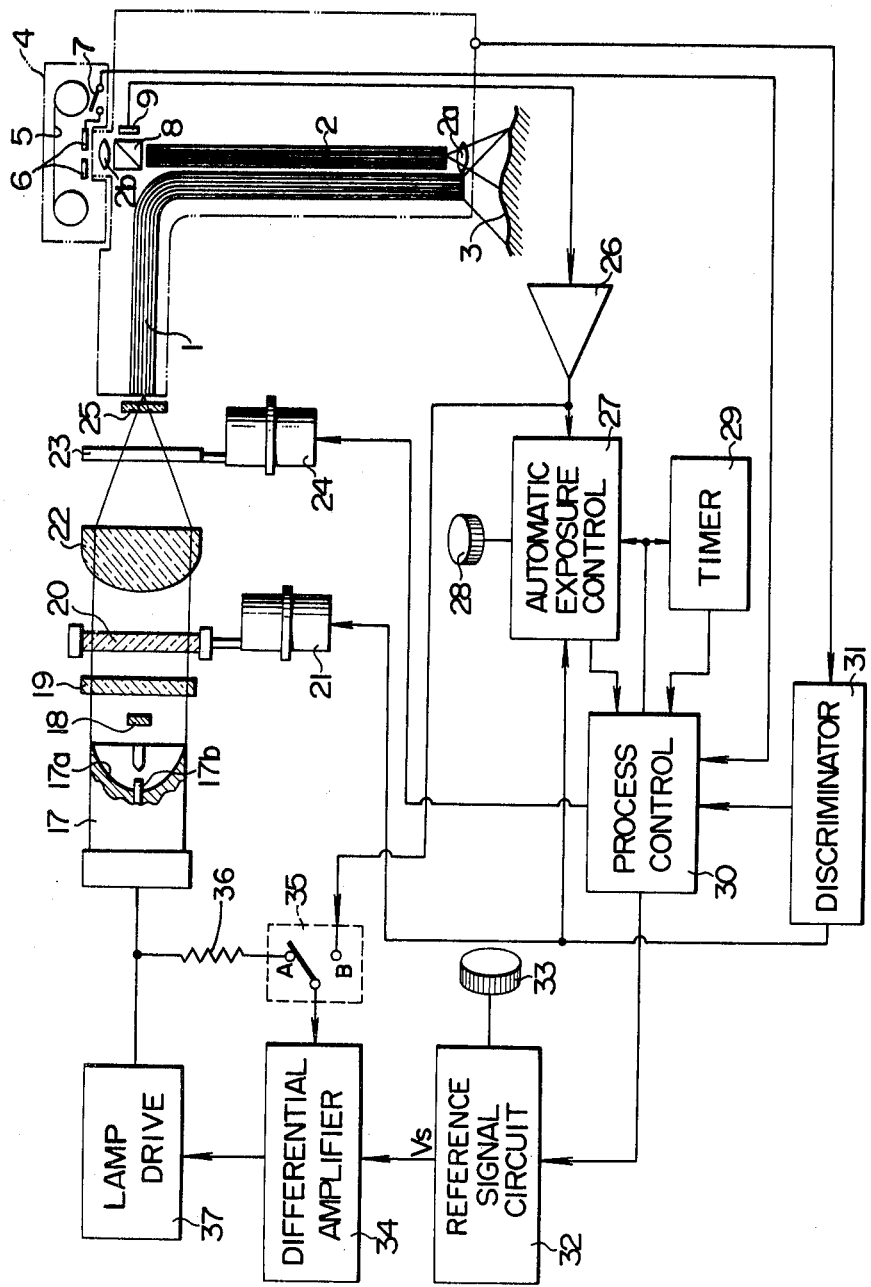
FIG. 4 is a schematic view, partly in block diagram, of the light source apparatus for an endoscope constructed in accordance with one embodiment of the invention.

Referring to FIG. 4, there is shown a light source apparatus for an endoscope according to the invention which is shown coupled with a fibrescope having an external still camera through a multi-function connector. However, it is to be understood that the apparatus may be equally coupled with gastrocameras shown in FIGS. 2 and 3.

Specifically, there is shown a source lamp 17 of a reduced size which is in the form of a Xenon short arc lamp having a paraboloidal mirror 17a, at the focus of which is placed arc electrode 17b. In this manner, an output flux from the lamp 17 is converted into parallel rays by the mirror 17a. A near axis flux shield member 18, a cold filter 19 and a color conversion filter 20 are disposed in sequence from left to right along the optical path. The shield member 18 serves to improve the light distribution in the output light passing through the light guide 1, preventing an excessively high light intensity in the central portion of the output beam. The purpose of the cold filter 19 is to remove unnecessary radiation components having longer wavelengths. The color conversion filter 20 is adapted to be driven by an electromagnetic solenoid 21 so as to be moved into the optical path when a gastrocamera is used, by energizing the solenoid with a signal from a discriminator 31 to be described later. A condenser lens 22 is also disposed in the optical path. The filters 19 and 20 are disposed at positions preceding the condenser lens 22 in order to reduce the loading per unit area of these filters, thereby preventing a cracking thereof. When the shield member 18 is located at the position shown, its adjustment is greatly facilitated than when it is placed in a narrower path following the condenser lens.

The condenser lens 22 functions to condense the parallel rays into a conical flux which is compatible with the angles of incidence for which they can be transmitted through the light guide 1. A light shield or electrical shutter 23 and a frosted glass plate 25 are disposed in the path of the conical flux. The shutter 23 is adapted to be driven by an electromagnetic solenoid 24 in order to terminate the exposure as will be described later. The frosted glass plate 25 is disposed adjacent to the focal plane of the condenser lens 22 to diffuse the flux impinging on the light guide 1 into a range of greater angles of incidence thereto. The frosted glass plate 25 also serves to prevent burning of the light guide 1 which may result from a direct imaging on the input end face thereof. The direct imaging can be prevented without the use of the frosted glass plate 25, by defocussing it, but this provides no diffusing effect, which achieves a greater range of angles for the incidence of the flux. The use of the frosted glass plate 25 is particularly effective when the lamp 17 has a small bright spot and the paraboloidal mirror 17a has a high precision.

The illumination flux thus collected is transmitted through the light guide 1 to illuminate an object 3 located within a cavity of a human body. An optical image formed by reflected light from the illuminated object 3 is transmitted through the image guide 2 and the half mirror 8 to be viewed or photographed. The half mirror 8 reflects part of the image in a direction at right angles to the direction of incidence, to be directed to a photoelectric transducer element 9. An output signal from the transducer element 9 is coupled through the multi-function connector 10 (see FIG. 1) to a d.c. amplifier 26 which is contained in the light source apparatus. An output of the amplifier 26 is fed to an automatic exposure control 27 associated with the still photography and is also fed to a differential amplifier 34 through a view mode switch 35. The differential amplifier 34 compares the signal fed through the switch 35 against an output reference signal Vs supplied by a reference signal circuit 32, and controls a lamp drive circuit 37 in accordance with any difference therebetween, thus varying the output light from the lamp 17. When the switch 35 is thrown to the position B, the illumination of an object being viewed can be controlled to a constant value by maintaining the output of the element 9 constant.

The magnitude of the reference signal Vs is established by a setting dial 33 disposed on a panel, not shown, of the light source apparatus, and assumes a value which is adjusted in accordance with a film speed selected. When the switch 35 is thrown to the position A, a voltage developed across a lamp current detecting resistor 36 is supplied to the differential amplifier 34 for comparison with the reference signal Vs. In this instance, the lamp current is maintained at a constant value which corresponds to the reference signal. As mentioned previously, this value can be chosen in accordance with the setting of the dial 33. In this manner, a current $I_{VAR}$ of the lamp during the view mode can be controlled to provide a constant illumination on the film surface or to a constant value.

When taking a still photograph, the output of the amplifier 26 is supplied to the circuit 27 for the automatic calculation of an exposure period. The operation of the circuit 27 is started and reset by the process control 30 which is in turn controlled by synchronizing signals fed from the discriminator 31 and the synchronizing contacts 7 of the camera 4. The circuit 27 operates to integrate an input voltage over time, and to produce an exposure stop signal whenever the integral reaches a given value. The magnitude of this value can be chosen by a setting dial 28 disposed on the panel, not shown, of the apparatus. At the same time with the initiation of operation of the circuit 27, a timer circuit 29 is activated to produce a timer signal after about one-half second. The circuit 29 may be formed by any of well known RC timer circuits. The exposure stop signal and the timer signal are both processed within the process control 30 to adjust the lamp current through the reference signal circuit 32 or to drive the solenoid 24 to operate the shutter 23.

Figure 5:
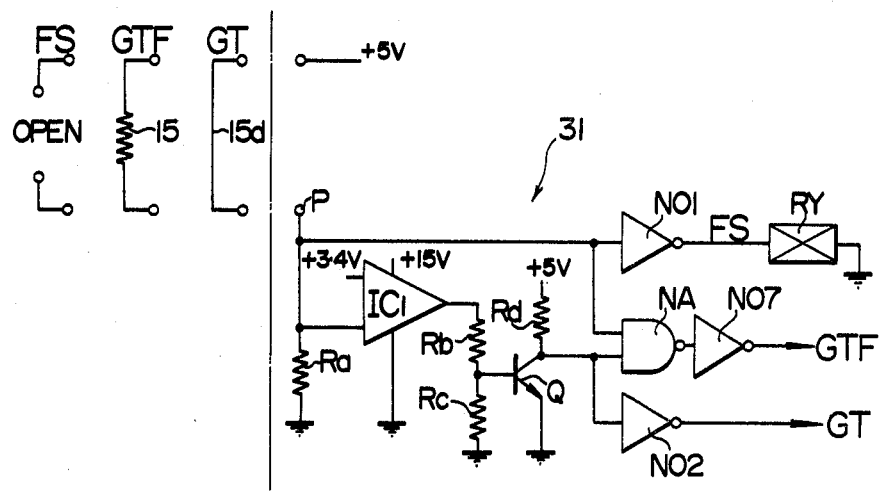
FIG. 5 is a circuit diagram of the discriminator shown in FIG. 4.

The detail of the discriminator 31 is shown in FIG. 5. In this Figure, abbreviations FS, GTF and GT represent the electrical feature of the respective endoscopes which is characterized by the elements 15, 15d incorporated therein. The abbreviation FS designates a fibrescope, GTS a gastrocamera with shutter and viewfinder and GT a gastrocamera without shutter and viewfinder. The combination of the discriminator 31 and the process control 30 enables an automatic establishment of a mode or circuit arrangement within the apparatus in response to a choice of a particular endoscope. The discriminator 31 includes a TTL gate IC1 formed by an integrated circuit, resistors Ra to Rd, transistor Q, NAND circuit NA, NOT circuits NO1, NO2 and NO7 and relay RY interconnected as shown.

The discriminator 31 includes an input terminal P to which a potential of nearly 0 V, 2.5 V or 5 V is applied in accordance with the electrical feature of the respective endoscopes when connected with the apparatus. The terminal P is connected with one input of TTL gate IC1 and NAND circuit NA and also with the input of NOT circuit NO1. The other input of TTL gate IC1 receives a reference voltage of 3.4 V which is chosen to enable a distinction between the varying potentials of the terminal P. The supply voltage to the TTL gate has an increased level in order to provide an output which is compatible with the logical levels.

In operation, when the potential of the terminal P is nearly 0 V, the output of NOT circuit NO1 goes high (H), indicating that the connected endoscope represents the "FS". At this time, NAND circuit NA produces a high output which is coupled to NOT circuit NO7 to provide a low output (L), indicating that the connected endoscope is not "GTF". The TTL gate IC1 produces an output of 0 V, whereby transistor Q is turned off providing a high input to NOT circuit NO2, which therefore produces a low output (L). Thus, the output of only NOT circuit NO1 is high when the potential of the terminal P is 0 V.

When the potential of the terminal P is 2.5 V, the input of NOT circuit NO1 as well as one input to NAND circuit NA is high, so that NOT circuit NO1 produces a low output. At this time, since the input voltage of 2.5 V is below the reference voltage of 3.4 V, TTL gate IC1 produces an output of 0 V, turning off transistor Q and supplying a high output to the input of NOT circuit NO2 and to the other input of NAND circuit NA. Thus, NOT circuit NO2 produces a low output. Since NAND circuit NA receives both high inputs, it produces a low output, which is inverted by NOT circuit NO7 to provide a high output. Thus, only NOT circuit NO7 produces a high output, indicating that the connected endoscope represents "GTF".

When the terminal P assumes a potential of 5 V, a high level signal is applied to the input of NOT circuit NO1 and one input of NAND circuit NO1 NA, with result that NOT circuit produces a low output. Since the input voltage of 5 V is higher than the reference voltage of 3.4 V, the gate IC1 produces an output voltage of +15 V which is equal to the magnitude of the supply voltage, whereby transistor Q is turned on, making the other input of NAND circuit NA and the input to NOT circuit NO2 low. Thus the circuit NA produces a high output which is inverted to a low level at the output of NOT circuit NO7, and only the circuit NO2 produces a high output, indicating that the connected endoscope represents "GT".

In the manner mentioned above, the discriminator 31 produces an output FS through NOT circuit NO1 when a fibrescope is connected therewith, an output GFT through NOT circuit NO7 when a gastrocamera having shutter and viewfinder is connected therewith, and an output GT through NOT circuit NO2 when a gastrocamera having no shutter and viewfinder is connected therewith. When a fibrescope is connected with the apparatus, the relay RY connected with the output of NOT circuit NO1 is energized in response to the output FS. When the relay RY remains deenergized, namely, when either gastrocamera is connected with the apparatus, the relay RY drives the solenoid 21 shown in FIG. 4 for bringing the color conversion filter 20 into the optical path. This operation is performed because when a film designated for use with a tungsten lamp is used, a Xenon lamp cannot be used to take a picture, thus requiring a reduction of the color temperature of the light source to the level of an incandescent lamp. In addition, the relay RY performs an automatic switching between constants used in the automatic exposure control 27 for the fibrescope and gastrocameras since a special constant may be employed with a film that is designated for use with the gastrocamera.

Figure 1:
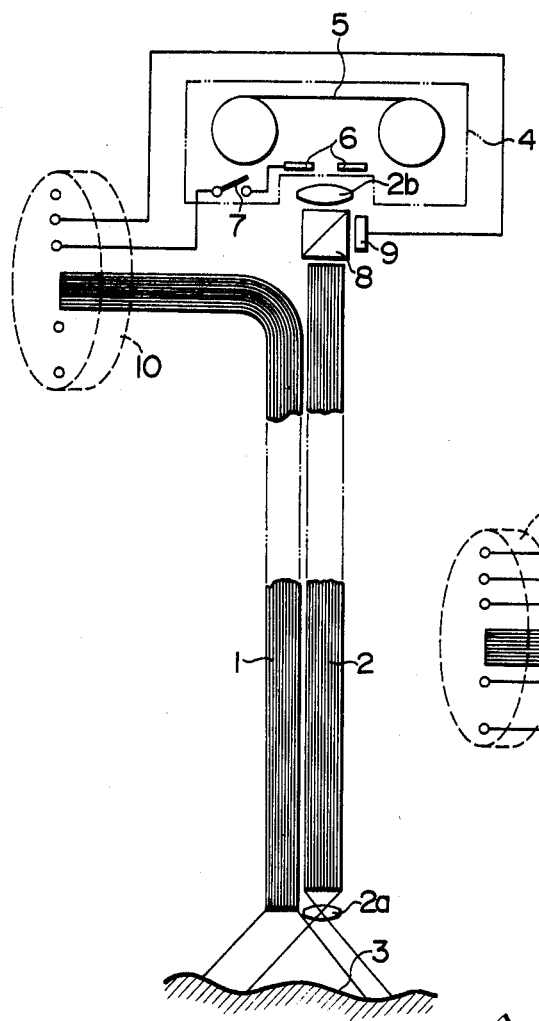
FIG. 1 is a schematic view illustrating a fibrescope with an external still camera.
Figure 2:
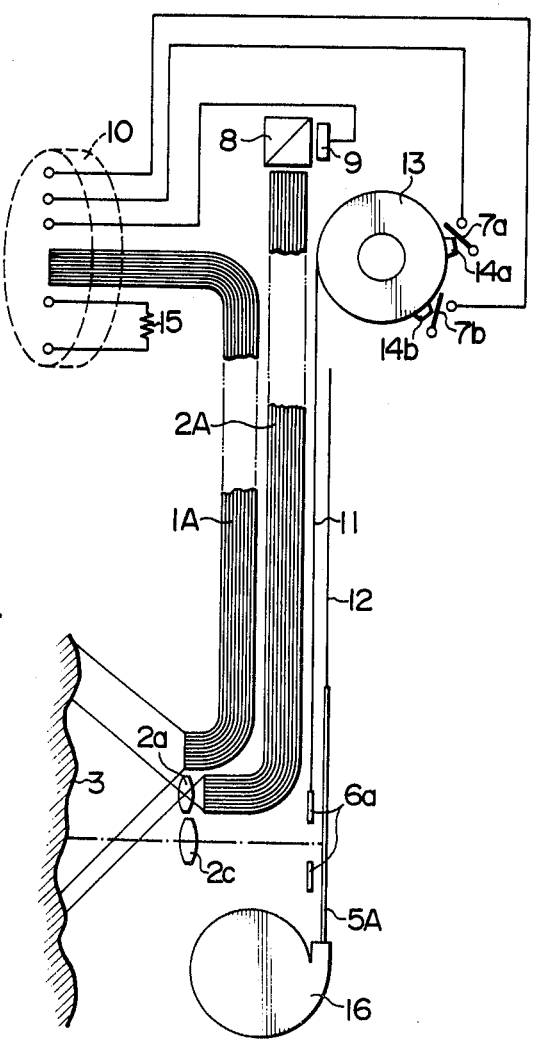
FIG. 2 is a schematic view of a gastrocamera having shutter and viewfinder.
Figure 6:
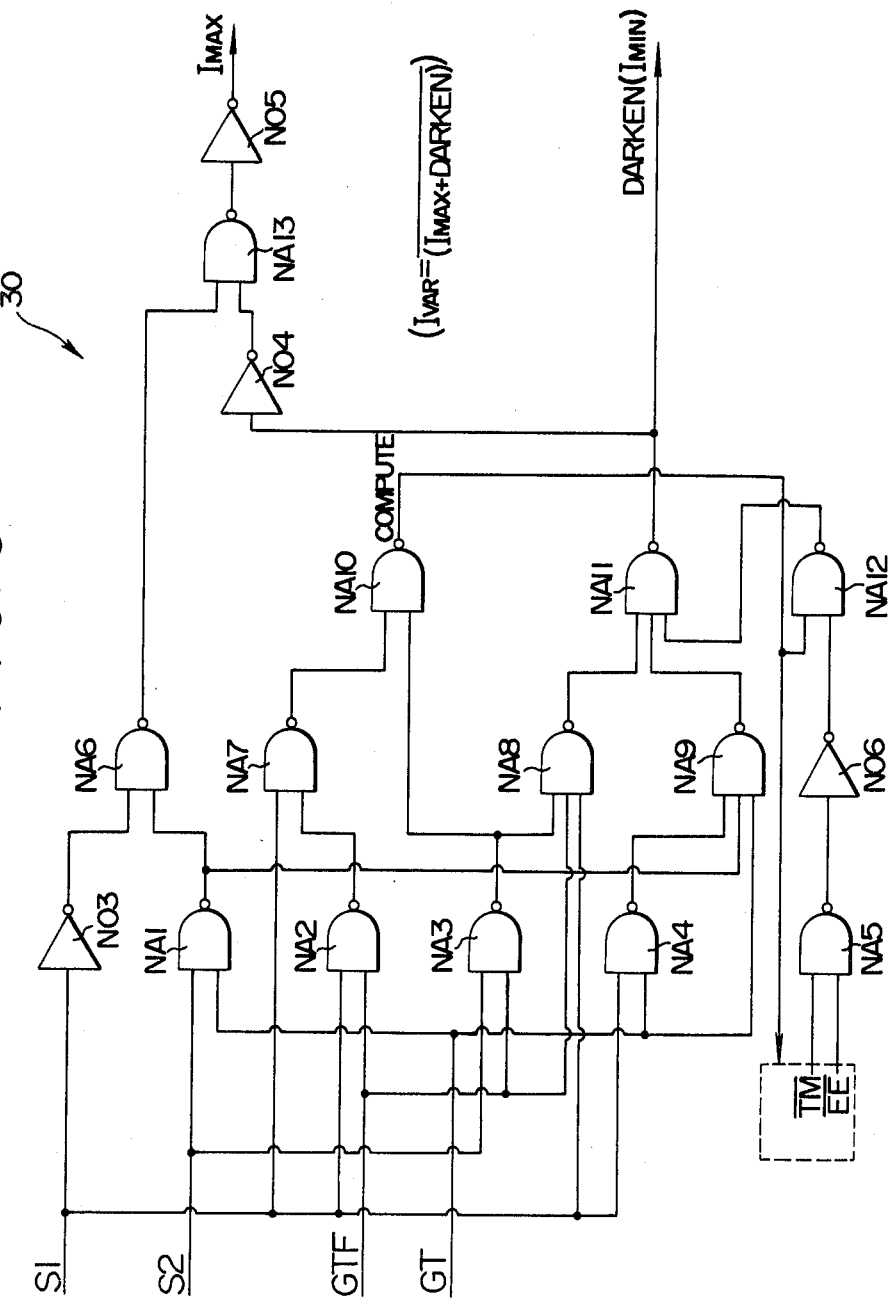
FIG. 6 is a block diagram of the process control shown in FIG. 4.

The detail of the process control 30 is shown in FIG. 6. As shown, it comprises NOT circuits NO3 to NO6 and NAND circuits NA1 to NA10 interconnected in the manner shown. Abbreviations used to designate certain signals shown in this Figure have the following meanings:

S1 . . . the closed condition of the synchronizing contacts 7 in response to either one of FS, GTF or GT (see FIGS. 1 to 3).

S2 . . . the closed condition of the synchronizing switch 7b or 7d in response to either GTF or GT (see FIGS. 2 and 3).

COMPUTE . . . a start command signal for initiating the automatic calculation of an exposure period for still photography.

EE . . . an exposure stop signal which is given as a result of the calculation initiated by COMPUTE.

TM . . . a timer signal produced during the calculation initiated by COMPUTE.

$I_{MAX}$ . . . a maximum lamp current command signal.

$I_{VAR}$ . . . a signal indicative of a mode in which a lamp current suitable for viewing purpose may be chosen at will.

DARKEN . . . a signal indicative of a mode in which a minimum lamp current is established and the shutter 23 (see FIG. 4) is operated to shield the output beam from the lamp.

FS . . . indicative of the fact that the connected endoscope represents a fibrescope.

GTF . . . indicative of the fact that the connected endoscope represents a gastrocamera having shutter and viewfinder.

GT . . . indicative of the fact that the connected endoscope represents a gastrocamera having no shutter and viewfinder.

It is to be understood that the circuit shown in FIG. 6 represents the implementation of the following Boolean expressions:

$$COMPUTE = GTF \cdot S2 + \overline{GTF} \cdot S1$$

This expression means that the calculation of the exposure period is initiated either i) in response to S2 whenever GTF is present or ii) in reponse to S1 whenever either FS or GT is present.

$$DARKEN = GTF \cdot S1 \cdot \overline{S2} + GT \cdot \overline{S1} \cdot \overline{S2} + COMPUTE \cdot (EE + TM)$$

This expression means that DARKEN is initiated i) in response to the presence of S1 and the absence of S2 for GTF, ii) in response to the absence of both S1 and S2 for GT or iii) in response to the signal COMPUTE and either signal EE or TM for any endoscope.

$$I_{MAX} = \overline{DARKEN} \cdot (S1 + GT \cdot S2)$$

This expression means that the maximum lamp current is established i) in response to the absence of the signal DARKEN and the presence of S1 for any endoscope or ii) in response to the absence of the signal DARKEN and the presence of S2 and GT.

$$I_{VAR} = \overline{DARKEN} \cdot \overline{(S1 + GT \cdot S2)}$$

This expression defines the time when a lamp current between the maximum and the minimum value can be chosen. Since $I_{VAR} + I_{MAX} + DARKEN = 1$, $I_{VAR} = \overline{(I_{MAX} + DARKEN)}$, indicating that $I_{VAR}$ represents the complement of the expression $(I_{MAX} + DARKEN)$. It should be understood that the signal COMPUTE is not a final output from the process control 30, which only produces signals DARKEN, $I_{MAX}$ and $I_{VAR}$ using NAND gate arrangement.

Figure 7:
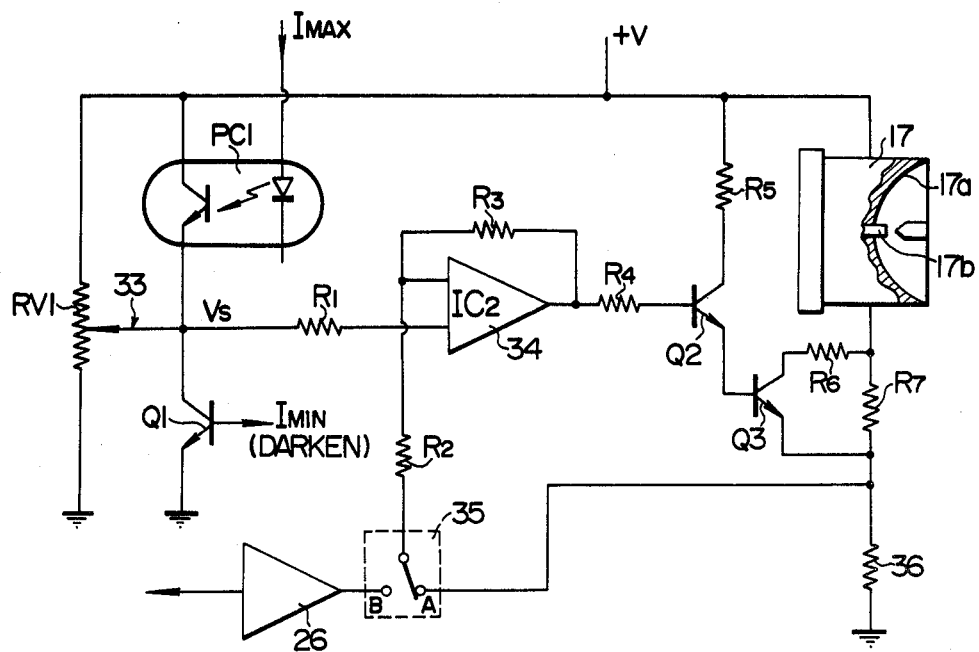
FIG. 7 is a circuit diagram of the lamp drive, differential amplifier and reference signal circuit shown in FIG. 4.

FIG. 7 shows the detail of the lamp drive circuit 37, differential amplifier 34 and reference signal circuit 32. It should be understood that this Figure illustrates only that part of the general circuit arrangement which is essential to the understanding of the present invention, and accordingly a starter, for example, is not shown. Referring to FIG. 7, since neither $I_{MAX}$ nor DARKEN ($I_{MIN}$) is normally present, photocoupler PC1 and transistor Q1 remain off, while a reference signal Vs is established by a variable resistor RV1. The reference signal Vs is supplied through input resistor R1 to one input of the differential amplifier 34. The amplifier 34 comprises an integrated circuit IC2, the other input terminal of which is connected through resistor R2 with the view mode switch 35 and also connected through resistor R3 with the output of the integrated circuit. The feedback signal coupled through the switch 35 represents either the photo signal from the output of the d.c. amplifier 26 or the lamp current signal fed by the lamp current detecting resistor 36. The output of the differential amplifier 34 is fed through resistor R4 and transistor Q2 to control the collector current of transistor Q3, controlling the lamp current in accordance with the position of the switch 35 or controlling it to a value which maintains the illumination of the object being viewed or photographed constant.

The transistors Q1 and Q2 and resistors R5, R6, R7 are chosen such that when transistor Q2 is on, the lamp current assumes a maximum value $I_{MAX}$ while when transistor Q2 is off, the lamp current is maintained to a value $I_{MIN}$ which is determined by the resistance of resistor R7. At the level $I_{MIN}$, the lamp is almost extinguished. It will be seen that when a signal $I_{MAX}$ is applied, the photocoupler PC1 raises the voltage level of the reference signal Vs to $+V$, turning on transistor Q2 to produce the maximum lamp current. On the other hand, when a signal $I_{MIN}$(DARKEN) is applied, transistor Q1 is turned on, reducing the reference signal Vs to zero, whereby transistor Q2 is turned off to produce the minimum lamp current. It is to be noted that the signals $I_{MAX}$ and $I_{MIN}$ cannot be simultaneously applied as a result of the logical arrangement shown in FIG. 6.

The operation of the apparatus will be described below.

1. Viewing operation

Viewing with an endoscope having a viewfinder, namely, with either a fibrescope or gastrocamera having a viewfinder, is achieved in either one of two modes established by the view mode switch 35 while employing a lamp current $I_{VAR}$. In the prior art practice, a constant level illumination has been achieved by driving a variable stop member into the optical path with a servo motor, but the arrangement included mechanical parts, which limited the speed of response, making it difficult to achieve a stable control. However, in accordance with the invention, the lamp current is electrically controlled, enabling a rapid response, permitting a stable condition to be reached within the order of milliseconds.

With an endoscope having no viewfinder, namely, a gastrocamera without viewfinder, the illumination is usually prevented in order to avoid the exposure of the film. However, the switch 7d (see FIG. 3) is temporarily closed to enable the illumination for the purpose of locating the camera position. This illumination takes place in the course of introducing the gastrocamera into the cavity of a human body, and the loss of the film is frequently limited to the initial one frame. Such operation is illustrated in the timing chart of FIG. 8. Describing the chart in terms of logical expressions, when neither synchronizing switches 7c (S1), 7d (S2) are closed during GT, the signal DARKEN is present to maintain the minimum lamp current $I_{MIN}$ and to maintain the shutter 23 (see FIG. 4) closed. However, when switch 7d (S2) is closed, the resulting condition is represented by $\overline{DARKEN} \cdot GT \cdot S2$, producing the signal $I_{MAX}$. The illumination takes place by opening the shutter 23. It should be obvious that for a normal viewing operation with other than GT, $I_{VAR}$ may assume any suitable value.

2. Photographing operation with fibrescope

The timing chart for the photographing operation with fibrescope is shown in FIG. 9. Upon shutter release of the external still camera, the shutter 6 thereof (see FIG. 1) is opened simultaneously, closing the synchronizing contacts 7 (FS·S1). In response thereto, the lamp current is changed from $I_{VAR}$ to $I_{MAX}$, producing a signal COMPUTE to initiate the automatic calculation of an exposure period. When the time integral of illumination or the photo signal reaches a given value, an exposure stop signal (command EE) is produced. In response thereto, a signal DARKEN is produced to reduce the lamp current from $I_{MAX}$ to $I_{MIN}$ and simultaneously closing the shutter 23. Then the exposure period, usually $\frac{1}{4}$ to $\frac{1}{2}$ second, established in the shutter of the external still camera 4 times out, automatically returning the shutter 6 and the synchronizing contacts 7. This produces $\overline{S1}$, which resets the entire circuit, whereby the lamp current resumes the value $I_{VAR}$ and the shutter 23 returns to an open condition, completing one cycle of operation. In this manner, a proper exposure is given to the film as illustrated in FIG. 9. The exposure is terminated at the end of the illumination because the space within the cavity is in total darkness.

It should be noted that in contradistinction to the prior art, the lamp current is switched from $I_{MAX}$ to $I_{MIN}$ in response to the exposure stop signal (EE). The operation of the electrical shutter 23 involves a time delay on the order of 5 to 8 msec with respect to the signal EE, so that unless the lamp current is reduced, an overexposure will be caused by the continued illumination during such time interval. In accordance with the invention, the ratio $I_{MAX}/I_{MIN}$ may be chosen equal to 6, for example, which reduces any resulting overexposure to a low value, for example, over a time interval of nearly 1 msec, as indicated by the shaded area in FIG. 9. This effectively contributes to increasing the available range of exposure periods. It should be noted that the exposure stop signal EE need not be produced within the apparatus, but that an electrical signal which is derived from AE (Automatic Exposure) camera or a so-called computer camera for interrupting the operation of a strobo unit may be utilized to function in the same way as illustrated in FIG. 9.

3. Photographing operation with gastrocamera having shutter and viewfinder

Figure 10:
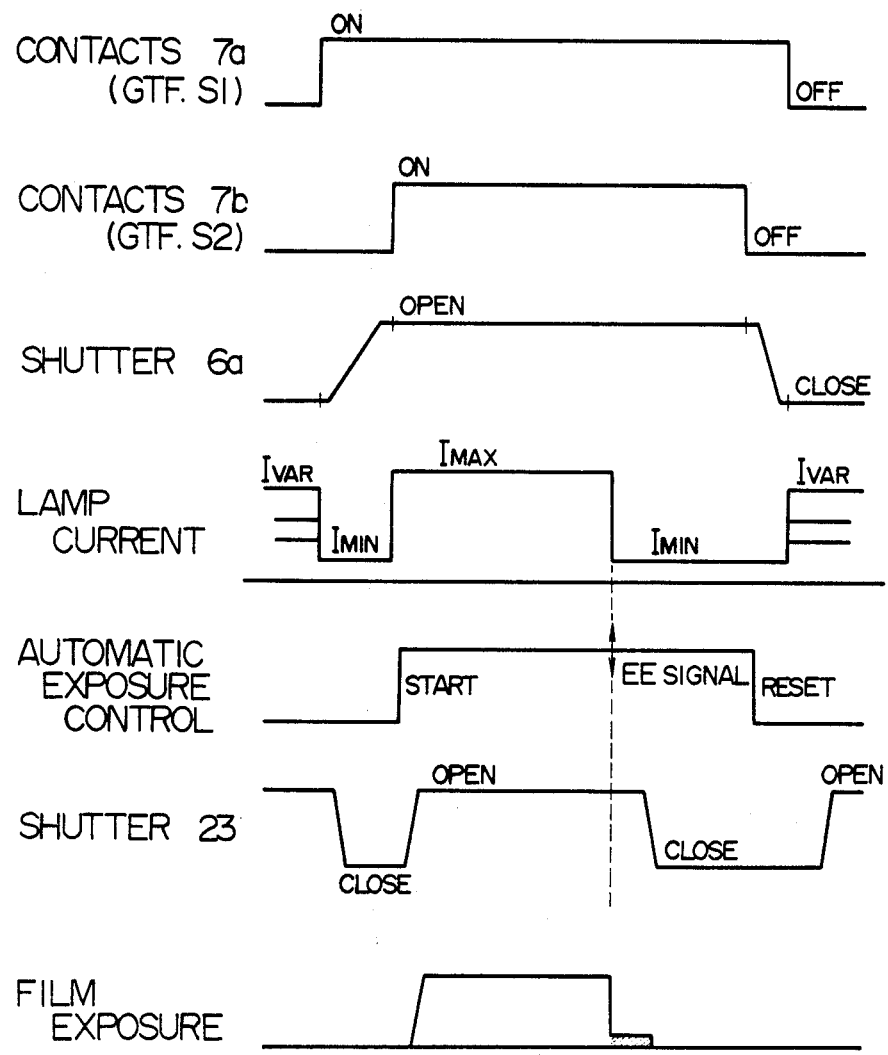

The timing chart for this photographing operation is shown in FIG. 10. Specifically, when a photographing operation is initiated, the synchronizing switch 7a (GTF·S1) is closed, changing the lamp current from $I_{VAR}$ to $I_{MIN}$. Simultaneously the shutter 23 is closed until the synchronizing switch 7b (GTF·S2) is closed in order to prevent any exposure to accommodate for the indefinite time interval between the signals S1 and S2. The shutter 23 will be closed several milliseconds later than S1, but in a gastrocamera, it will take a time interval on the order of 10 to 20 milliseconds from the closure of the switch 7a until the camera shutter 6a begins to open, so that an exposure may be initiated in the course of movement of the shutter 6a, resulting in a deviation from a calculated exposure period or an overexposure caused on one-half of an image frame.

When S2 is produced upon complete opening of the shutter 6a, the lamp current is switched from $I_{MIN}$ to $I_{MAX}$ and the shutter 23 is opened. The automatic calculation of an exposure period is initiated by the signal COMPUTE. Subsequently, the process proceeds in the similar manner as described above in connection with the fibrescope. However, because there is no exposure period established as in the external still camera, a timer is provided to produce a timer signal TM after 500 milliseconds, in addition to the exposure stop signal EE, thereby permitting the exposure to be terminated by one of these signals whichever occurs first.

4. Photographing operation with gastrocamera having no shutter and viewfinder

Figure 11:
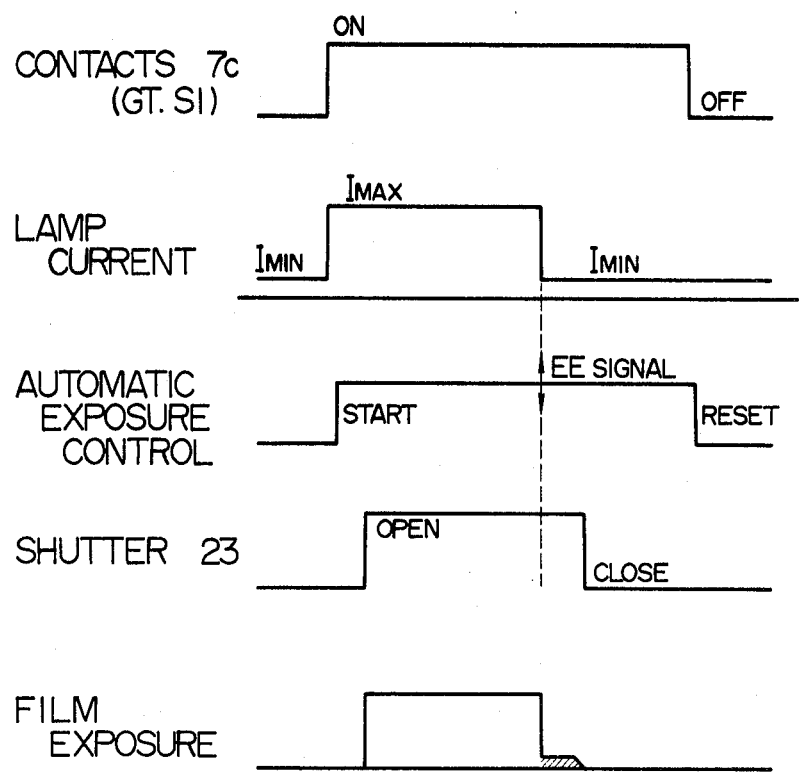
Figure 4:
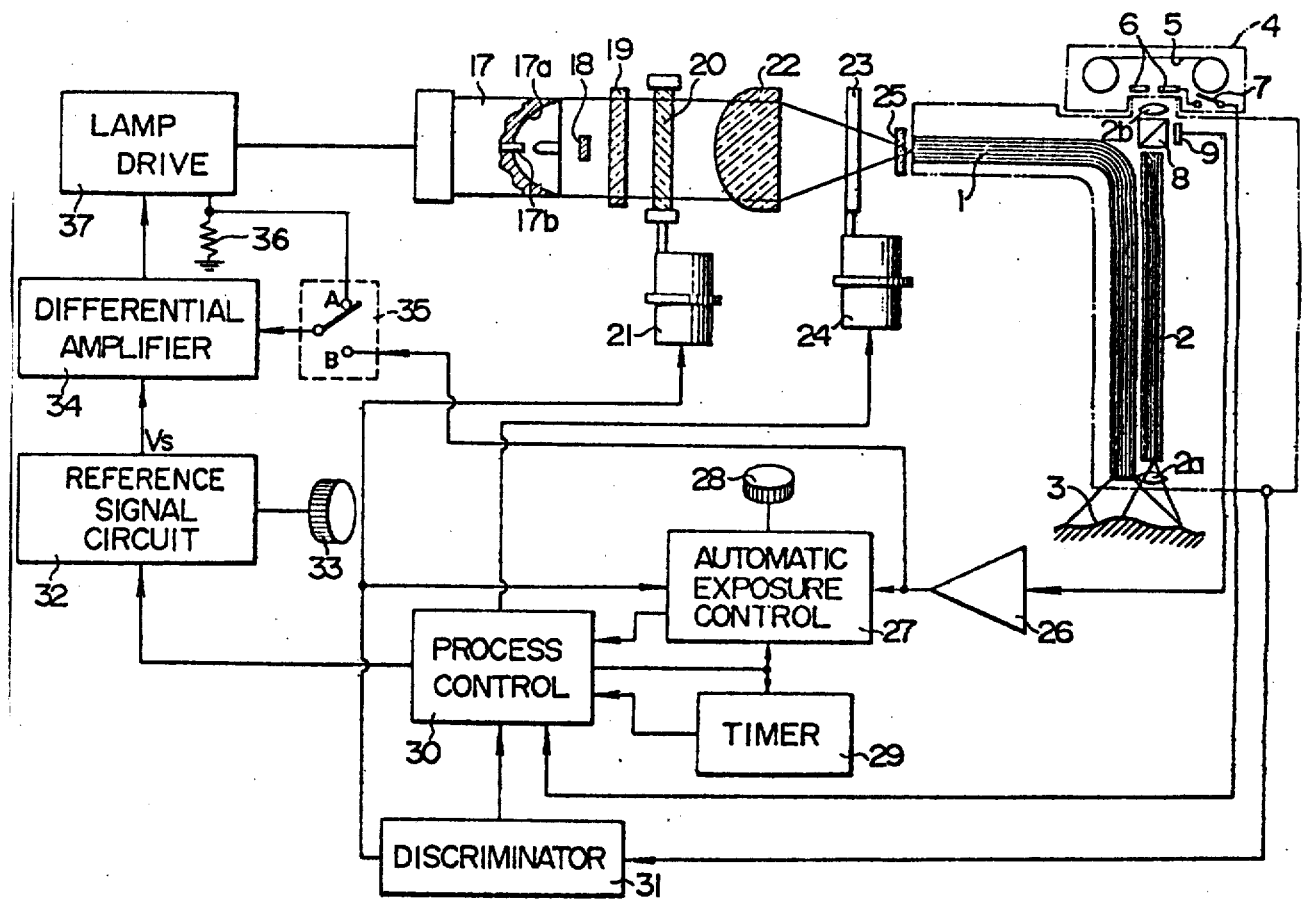

The timing chart for this operation is shown in FIG. 11. Since a photographing operation usually does not take place, the shutter 23 remains closed and the lamp current is maintained at the level $I_{MIN}$. When a photographing operation is initiated, the synchronizing switch 7c (GT·S1) is closed to change the lamp current from $I_{MIN}$ to $I_{MAX}$ and open the shutter 23. The automatic calculation of an exposure period is initiated by the signal COMPUTE. Subsequent operation until the exposure is terminated is similar as in the previous photographing operations except that the lamp current is maintained at the minimum level $I_{MIN}$ after the termination of the exposure and the shutter 23 remains closed even if the synchronizing switch 7c is turned off, thus maintaining a dark condition.

What is claimed is:

1. A connector assembly for use with endoscopes and the like especially adapted for accomodating a variety of different types of endoscopes including fiberscopes and gastrocameras with and without a shutter and a viewfinder, each of said endoscopes including a branch circuit having an electrical impedance identifying the type of endoscope, said connector assembly comprising:

discriminator means separately connectable with the branch circuits of said endoscopes, said descriminator means being responsive to the electrical impedance of the branch circuit to which it is connected for developing an electrical signal representative of the type of endoscope to which it is connected.

2. The connector assembly of claim 1, wherein said discriminator means includes comparator means for comparing the impedance value of said branch circuit against a reference level.

3. A connector assembly for use with endoscopes and the like especially adapted for accomodating a variety of different types of endoscopes including fiberscopes and gastrocameras with and without a shutter and a viewfinder, each of said endoscopes including a branch circuit having an electrical impedance identifying the type of endoscope, said connector assembly comprising:

discriminator means separately connectable with the branch circuits of said endoscopes for developing an electrical signal representative of the type of endoscope to which it is connected;

lamp means;

shutter means positioned between said lamp means and the endoscope to which said discriminator means is connected; and control means responsive to said electrical signal developed by said descriminator means for selectively controlling said lamp means and said shutter means.

4. The connector assembly of claim 3, wherein said discriminator means includes comparator means for comparing the impedance value of said branch circuit against a reference level.

5. The connector assembly of claim 3, wherein said control means illuminates said lamp means and opens said shutter means for a predetermined time interval, said shutter means being closed and the lamp illumination being reduced to a predetermined minimum level upon termination of said predetermined time interval.

6. The connector assembly of claim 5, further comprising adjustable means for maintaining the illumination of said lamp means at an adjusted value between a maximum level and said predetermined minimum level; and means responsive to an exposure period for shifting the illumination of said lamp means to said maximum level upon initiation of said exposure period and for shifting the illumination level to said minimum level upon termination of said exposure period.

7. The connector assembly of claim 6, further comprising means responsive to the branch circuit impedance of an endoscope having a shutter and to the closure of said shutter for resetting the lamp illumination to said adjusted value between said predetermined minimum level and said maximum level.

8. A light source apparatus for endoscopes and the like comprising a discharge lamp as a light source, an optical system for causing an output light beam from the lamp to impinge on a bundle of optical fibres of an endoscope which transmit illuminating light, lamp current control means for selectively establishing a lamp current at one of three levels comprising a maximum level, a minimum level and an intermediate level, switching means for switching the lamp current from a normal value to the maximum level in synchronism with the initiation of an exposure given to a photographic film, means for initiating the calculation of an exposure given to the film in synchronism with the initiation of the exposure thereto and for producing an exposure stop signal when the exposure given to the film reaches a given value, means for switching the lamp current from the maximum level to the minimum level and for moving a light shield member into the path of said illuminating light in response to the exposure stop signal, the light source apparatus being adapted to be connected with any one of a variety of endoscopes using different exposure techniques and synchronization techniques, including a fibrescope with external camera, a gastrocamera having shutter and viewfinder, and a gastrocamera having no shutter and viewfinder, and mode selection means responsive to an electrical feature of the particular endoscope connected with the apparatus to establish automatically a suitable exposure and synchronization technique for a selected endoscope, said mode selection means being operable when the fibrescope is connected with the apparatus for a normal viewing operation to establish the lamp current at an intermediate level, said mode selection means being operable when a gastrocamera having shutter and viewfinder is connected with the appartus for a normal viewing operation to establish the lamp current at an intermediate level and operable to interrupt the illumination in the course of opening of the shutter by moving the light shield member into the path of illuminating light, said mode selection means being operable when a gastrocamera having no shutter and viewfinder is connected with the apparatus to establish the lamp current at the minimum level and to interrupt the illumination by moving the light shield member into the path of illuminating light.

9. An apparatus according to claim 8 in which the intermediate level can be chosen either to a constant value or to a value which maintains the illumination of a film surface constant.

10. An apparatus according to claim 8 in which the calculation of the exposure given to the film is performed by automatically selecting a suitable constant corresponding to the connected endoscope.

11. An apparatus according to claim 8 in which the mode selection means includes an optical filter, and an electromagnetic solenoid which is operative to drive the filter into the path of illuminating light when it is energized, thus automatically controlling the movement into and out of the path in accordance with the type of the endoscope connected with the apparatus.

12. An apparatus according to claim 8 in which the mode selection means includes a timer for terminating the exposure in a given time interval, the timer being effective to produce an exposure stop signal during a photographing operation of the gastrocamera having shutter and viewfinder, thereby terminating the exposure when it continues over a prolonged period of time.

13. An apparatus according to claim 8 in which the mode selection means is responsive to a synchronizing switch of the camera when a gastrocamera having no shutter and viewfinder is connected with the apparatus to remove the light shield member out of the path of illuminating light and to maintain the lamp current at the maximum level for a selected time interval in order to locate the camera position.

14. An apparatus according to claim 8 in which the light shield member comprises an electrical shutter.

15. An apparatus according to claim 8 in which the electrical feature is formed by an electrical element.

* * * * *

UNITED STATES PATENT AND TRADEMARK OFFICE
CERTIFICATE OF CORRECTION

PATENT NO. : 4,153,356                    Page 1 of 2
DATED      : May 8, 1979
INVENTOR(S) : Hiroyuki Hama It is certified that error appears in the above-identified patent and that said Letters Patent are hereby corrected as shown below:

In the drawings, Sheet 3 of 8, Figure 4 should appear as shown on the attached sheet.

Signed and Sealed this

Sixth Day of November 1979

[SEAL]

Attest:

RUTH C. MASON  
Attesting Officer

LUTRELLE F. PARKER  
Acting Commissioner of Patents and Trademarks